(12) United States Patent
Shapley et al.

(10) Patent No.: US 10,272,197 B2
(45) Date of Patent: Apr. 30, 2019

(54) THERAPEUTIC PRODUCT DELIVERY DEVICE WITH OCCLUSION DETECTION VIA ELECTRIC CONTACTS

(71) Applicant: Cellnovo Limited, Swansea (GB)

(72) Inventors: Julian Shapley, Swansea (GB); Matthew Powell, Swansea (GB); Nici Gittens, Swansea (GB); Neil Thomas, Swansea (GB)

(73) Assignee: Cellnovo Limited, Swansea (GB)

( * ) Notice: Subject to any disclaimer, the term of this patent is extended or adjusted under 35 U.S.C. 154(b) by 284 days.

(21) Appl. No.: 15/114,838

(22) PCT Filed: Jan. 30, 2015

(86) PCT No.: PCT/GB2015/050247
§ 371 (c)(1),
(2) Date: Jul. 27, 2016

(87) PCT Pub. No.: WO2015/114369
PCT Pub. Date: Aug. 6, 2015

(65) Prior Publication Data
US 2016/0339174 A1   Nov. 24, 2016

(30) Foreign Application Priority Data

Jan. 30, 2014  (GB) .................................. 1401588.7

(51) Int. Cl.
*A61M 5/168* (2006.01)
*A61M 5/50* (2006.01)
(Continued)

(52) U.S. Cl.
CPC ....... *A61M 5/16831* (2013.01); *A61B 5/0002* (2013.01); *A61B 5/1118* (2013.01);
(Continued)

(58) Field of Classification Search
CPC ......... A61M 2005/14268; A61M 2005/16863; A61M 2205/18; A61M 2205/3341;
(Continued)

(56) References Cited

U.S. PATENT DOCUMENTS

2003/0073952 A1*  4/2003  Flaherty ............ A61M 5/14248
604/151
2010/0137784 A1   6/2010  Cefai et al.
(Continued)

FOREIGN PATENT DOCUMENTS

CA        2863379      8/2013
EP        1762263      3/2007
(Continued)

OTHER PUBLICATIONS

U.K. Intellectual Property Office, GB Application No. GB 1401588.7, "Search Report under Section 17(5)" dated Aug. 17, 2015, 3 pages.
(Continued)

*Primary Examiner* — Nathan R Price
*Assistant Examiner* — Anh Bui
(74) *Attorney, Agent, or Firm* — Kang S. Lim (57) ABSTRACT

A therapeutic product delivery device is described, which comprises a circuit layer, an actuator layer carrying an actuator, an occlusion detection layer (118), and a valve layer, through which a therapeutic product is conveyed by the action of the actuator. A plurality of conductive pins (155) extend from the circuit layer through or to each of the actuator layer, the occlusion detection layer and the valve layer, the conductive pins aligning the layers with each other. The occlusion detection layer comprises a plurality of contacts, each electrically connected to a respective one of the conductive pins, the contacts being provided at a detection region at which the therapeutic product is deposited in
(Continued)

the event of a blockage. A blockage inhibiting the therapeutic product from being conveyed to the patient is detected when therapeutic product deposited in the detection region provides an electrical connection between the contacts. The conductive pins therefore provide at least two functions; firstly they align the layers of the cartridge (at assembly and during use), and a secondly they provide a conductive route between the circuit layer and the occlusion layer, permitting therapeutic product deposited at the occlusion layer to be able to complete an electric circuit with the circuit layer to enable occlusion detection.

10 Claims, 6 Drawing Sheets (51) Int. Cl.
*A61M 5/14* (2006.01)
*A61B 5/145* (2006.01)
*A61M 5/142* (2006.01)
*A61B 5/00* (2006.01)
*A61B 5/11* (2006.01)
*A61M 5/172* (2006.01)

(52) U.S. Cl.
CPC ........ *A61B 5/14532* (2013.01); *A61B 5/6898* (2013.01); *A61M 5/1413* (2013.01); *A61M 5/14224* (2013.01); *A61M 5/14244* (2013.01); *A61M 5/168* (2013.01); *A61M 5/172* (2013.01); *A61M 5/5086* (2013.01); *A61B 2562/227* (2013.01); *A61M 2005/14268* (2013.01); *A61M 2005/16863* (2013.01); *A61M 2205/18* (2013.01); *A61M 2205/3341* (2013.01); *A61M 2205/3553* (2013.01); *A61M 2205/3569* (2013.01); *A61M 2205/3576* (2013.01); *A61M 2205/3584* (2013.01); *A61M 2205/8206* (2013.01); *A61M 2230/63* (2013.01)

(58) Field of Classification Search
CPC ........ A61M 2205/8206; A61M 5/1413; A61M 5/168; A61M 5/16831; A61M 5/5086
See application file for complete search history.

(56) References Cited

U.S. PATENT DOCUMENTS

2011/0316562 A1 12/2011 Cefai et al.
2016/0184517 A1* 6/2016 Baek ................. A61M 5/14244
604/111

FOREIGN PATENT DOCUMENTS

| | | |
|---|---|---|
| EP | 1852703 | 11/2007 |
| EP | 2353628 | 8/2011 |
| GB | 2443261 | 4/2008 |
| GB | 1401588.7 | 1/2014 |

OTHER PUBLICATIONS

European Patent Office, "Notification of Transmittal of the ISR and the Written Opinion of the International Searching Authority, or the Declaration," in PCT Application No. PCT/GB2015/050247, dated May 8, 2015, 15 pages.

* cited by examiner

THERAPEUTIC PRODUCT DELIVERY DEVICE WITH OCCLUSION DETECTION VIA ELECTRIC CONTACTS

CROSS-REFERENCE TO RELATED APPLICATIONS

The present application is a United States National Stage entry under 35 U.S.C. § 371 of International Application No. PCT/GB2015/050247 filed Jan. 30, 2015, designating the United States of America and published in English on Aug. 6, 2015, which in turn claims priority to Great Britain Application No. 1401588.7, filed Jan. 30, 2014, each of which is incorporated herein by reference in their entirety.

FIELD OF THE INVENTION

The present invention relates to a therapeutic product delivery device.

BACKGROUND TO THE INVENTION

Conventionally, Type 1 diabetes has been treated with daily insulin injections. However, this inevitably results in insulin levels that do not match the normal and rapid changes in blood glucose which occur in a patient throughout the day. On the one hand, insufficient insulin and high glucose levels lead to immediate symptoms and contribute to long-term complications. On the other hand, too much insulin may result in too little blood sugar leading to loss of consciousness and convulsions. As an alternative to injections, insulin pump therapy is intended to mimic the normal physiology of the healthy pancreas. Unlike multiple daily insulin injections, an insulin pump is able to provide a constant background infusion of insulin that can be adjusted according to individual need, compensating for daily activity and exercise routines. The pump may also be programmed to deliver bolus doses of insulin to address the big glucose swings in the blood that would otherwise result from eating and drinking. By mimicking the natural physiology of the pancreas, insulin pump therapy aims to maintain a constantly normal blood glucose level; avoiding the highs that are associated with meals or the lows that come from too much insulin.

It is important for the patient to know that the insulin pump is successfully delivering insulin to his or her body. It is therefore important for the patient to be made aware when a blockage is preventing this.

SUMMARY OF THE INVENTION

According to an aspect of the present invention, there is provided a therapeutic product delivery device, comprising:
 a circuit layer;
 an actuator layer carrying an actuator;
 an occlusion detection layer; and
 a valve layer, through which a therapeutic product is conveyed by the action of the actuator;
 a plurality of conductive pins extending from the circuit layer through or to each of the actuator layer, the occlusion detection layer and the valve layer, the conductive pins aligning the layers with each other;
 wherein the occlusion detection layer comprises a plurality of contacts, each electrically connected to a respective one of the conductive pins, the contacts being provided at a detection region at which the therapeutic product is deposited in the event of a blockage;
 and wherein a blockage inhibiting the therapeutic product from being conveyed to the patient is detected when therapeutic product deposited in the detection region provides an electrical connection between the contacts.

The conductive pins therefore provide at least two functions; firstly they align the layers of the cartridge (at assembly and during use), and a secondly they provide a conductive route between the circuit layer and the occlusion layer, permitting therapeutic product deposited at the occlusion layer to be able to complete an electric circuit with the circuit layer to enable occlusion detection. As an additional benefit, a leak within the device may electrically connect together the conductive pins thereby triggering an alarm as if a blockage had been detected. Advantageously, there is no need to provide for separate structures for mechanically connecting and aligning the layers of the device and electrically connected a circuit layer to an occlusion layer.

Preferably, the valve layer comprises an outlet valve via which the therapeutic product is required to pass to reach the patient, and a break-through valve through which the therapeutic product is only able to pass in the event that a blockage inhibits the therapeutic product from reaching the patient, the therapeutic product passing through the break-through valve being deposited at the detection region. The break-through valve is preferably disposed in series with, and at the exit of, the outlet valve. Preferably, a channel is provided for carrying the therapeutic product from the break-through valve to the detection region.

Control circuitry may be responsive to therapeutic product being detected in the detection region to trigger an alarm at the therapeutic product delivery device and/or at a control device. The control circuitry may be responsive to therapeutic product being detected in the detection region to discontinue the operation of the actuator. Preferably, the control circuitry is separate from the circuit layer (which itself merely provides the electrical connection required by the control circuitry).

Preferably, the occlusion detection layer and the valve layer are sealed from the circuit layer by a seal layer. In this case, it is even more advantageous to provide a double function for the conductive pins, since it is desirable to minimise the number of points of penetration through the seal layer to reduce the risk of a leak from within the sealed area to the actuator or circuit layer.

Preferably, the therapeutic product delivery device comprises a reservoir for storing the therapeutic product, and the valve layer comprises a pumping chamber from which the therapeutic product is pumped by action of the actuator. In this case, the pumping chamber is refilled from the reservoir via an inlet valve.

While it will be appreciated that the conductive pin arrangement will be beneficial for any layered structure comprising the elements mentioned above, preferably the circuit layer, the actuator layer, the occlusion detection layer and the valve layer are disposed in this order.

Preferably, the delivery device comprises the circuit layer, the actuator layer, the occlusion detection layer and the valve layer in a cartridge part. In this case, the delivery device comprises a device body part comprising a battery and control circuitry for applying an electric current to the actuator via the circuit layer. The cartridge part and the main body part are preferably releasably engageable with respect to each other.

Various other aspects and features of the present invention are described in the embodiments which follow.

DETAILED DESCRIPTION

The invention will now be described by way of example with reference to the following Figures in which.

SYSTEM

Figure 1:
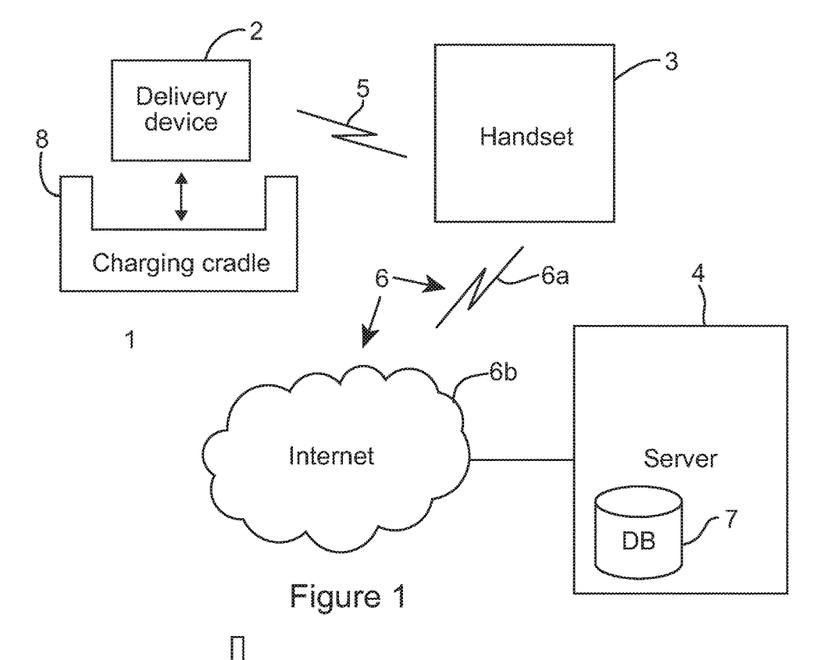
FIG. 1 shows a schematic view of a drug delivery system.

Referring to FIG. 1, a drug delivery system 1 is schematically illustrated. The drug delivery system 1 in this case delivers insulin to a patient. However, it will be appreciated that embodiments of the present invention may be appropriate for delivering drugs other than insulin. The system 1 comprises a delivery device 2 which is worn on the patient's body, a handset 3 (which may appear similar to a smartphone) for controlling the delivery device 2, and a server 4. The delivery device 2 and the handset 3 are able to communicate via a first wireless connection 5, for example a lower power ANT radio connection. The handset 3 and the server 4 are able to communicate via a second wireless connection 6, for example a GPRS mobile data connection 6a and the Internet 6b. The server 4 comprises a patient database 7 for storing patient medical information and other information about the patient. Both the delivery device 2 and the handset 3 are powered by rechargeable batteries. Also shown in FIG. 1 is a charging cradle 8 into which the delivery device 2 is inserted in order to charge the delivery device 2.

Delivery Device

Figure 2:
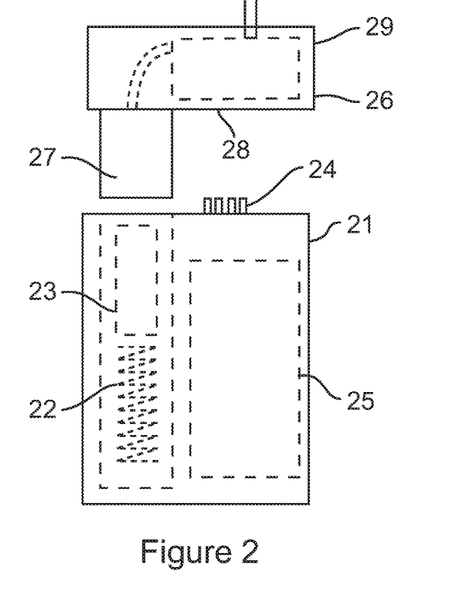
FIG. 2 shows a schematic view of a drug delivery device.

The delivery device comprises two parts, which are detachable from each other, as shown schematically in FIG. 2. The first of the two parts is a body 21, which contains a spring 22, a biasing member 23 including a displacement sensor (for example as described in US2011/0316562), and a set of contact pins 24 for providing an electrical connection with the second part. The body 21 also comprises a battery, control circuitry and a transceiver for communicating with the handset, which are not separately shown in FIG. 2 in the interests of clarity, but are generally represented by element 25. The second of the two parts is a disposable insulin cartridge 26, which comprises a reservoir 27 of insulin, contact pads 28 for providing an electrical connection with the body 21 via the pins 24, a pumping device (a wax actuator, for example as described in GB2443261) for pumping the insulin from the reservoir 27 into the patient's body, and a valve arrangement (for example as described in US2010/0137784). The pumping device and valve arrangement are not separately shown in FIG. 2 in the interests of clarity, but are generally represented by element 29. It will be understood that the body 21 of the delivery device is reusable, while the disposable cartridge 26 is intended to be removed and disposed of when the reservoir 27 has been depleted, or when the cartridge has passed its use by date, or if it develops a fault. A new cartridge can then be engaged with the body 21. While it is preferable that the cartridge is disposable, it will be appreciated that, in principle, the cartridge may be refilled and reused again rather than being disposed of. However, even in this case the cartridge should be removable from the body so that a new (full) cartridge can be used while the original cartridge is being refilled.

In use, the body 21 and the cartridge 26 of the delivery device 2 are physically and electrically connected. The electrical connection is via the pins 24 and pads 28. The physical connection may be provided by clips or any other releasable engagement mechanism (not shown). The control circuitry in the body 21 is responsive to control signals received from the handset 3 via the wireless connection 5 to draw current from the battery and apply an electrical current via the pins 24 and the pads 28 to activate the pumping device within the cartridge 26 to draw fluid from the reservoir 27 through the valve arrangement and out of the delivery device 2 to a patient's body. The rate of delivery of the therapeutic product can be controlled by the control circuitry to achieve a particular basal delivery rate, or bolus dose, by controlling the amount and timing of electrical current to the pumping device. Although the basal rate is set by the handset, once set the delivery device 2 is able to maintain the set basal rate with no further communication from the handset 3. As can be seen in FIG. 2, when the body 21 and the cartridge 26 are in engagement, the reservoir 27 is received within the body 21, displacing the biasing member (and displacement sensor) 23 and compressing the spring 22. The compressed spring applies a biasing force to a base of the reservoir 27 via the biasing member 23. The biasing force does not in isolation force insulin from the reservoir 27 through the valve arrangement and into the patient's body, but when combined with the pumping action of the pumping device, the biasing force pressurises the insulin in the reservoir 27 to refill a pumping chamber in advance of each pumping action. It is the pumping action which drives a controlled amount of insulin from the pumping chamber through an outlet valve and to the patient's body. The reservoir takes the form of a cylinder having a first end from which insulin is drawn under the action of the pump, and a second end opposite to the first end at which the (moveable) base is provided. The base of the reservoir moves inwardly of the reservoir (to effectively decrease the size of the reservoir) as the insulin is pumped from the reservoir, under the biasing force provided by the biasing member 23. The position of the biasing member 23 is dependent on the current fill state of the reservoir—that is, how much insulin is remaining in the reservoir. The position of the biasing member 23, and thus the base of the reservoir 27, is determined by the displacement sensor. The displacement sensor is therefore able to generate a signal indicative of the remaining quantity of insulin in the reservoir. By monitoring the change in the remaining quantity of insulin with respect to time, an actual rate of insulin delivery can be determined. This can be used by the control circuitry to apply corrections to the actual delivery rate by adapting the amount and/or timing of electrical current to the pumping device. The quantity of insulin remaining in the reservoir is transmitted to the handset 3, where it can be displayed to the patient and used as an indicator of when the patient should change the current cartridge for a new cartridge. The control circuitry in the body 21 may also transmit an indication of current battery level to the handset, so that the patient is made aware of when the battery requires recharging.

The delivery device also contains an activity monitor to track exercise (not shown). Exercise can have a significant effect on the amount of insulin needed for good control, so tracking exercise accurately is an important part of effective diabetes management. The activity monitor uses a sensor in the delivery device to detect movement of the delivery device, which can be used to infer when the user is engaged in physical activity. The detected activity is then wirelessly communicated to the handset via the wireless connection 5, where the handset (and the server) is able to track and record the patient's activity. Through an online portal to the server, the patient and permitted medical professionals are able to compare activity peaks with blood glucose to identify how activity is influencing the patient's need for insulin. This can in turn be used to program the handset with appropriate dosages for the patient.

Due to the fact that the patient interfaces with the handset rather than the delivery device itself, the delivery device is able to be made small and discreet, and is provided without buttons or a physical connection to a control unit.

Handset

Figure 3:
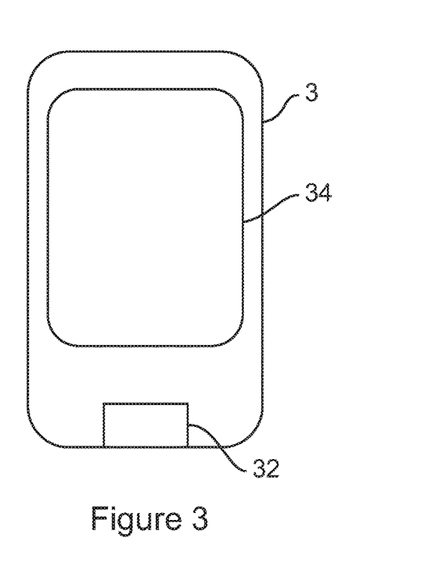
FIG. 3 shows a schematic view of a handset for controlling the drug delivery device of FIG. 2.

The handset 3 comprises two transceivers. The first transceiver is for communicating with the delivery device via the first wireless connection 5, while the second transceiver is for communicating with the server 4 via the second wireless connection 6. The handset also comprises a processor for running control software. The control software monitors the patient's condition and reports it to the central server 4, and controls the delivery of insulin doses to the patient by transmitting control signals to the delivery device 2. The handset 3 also comprises a touch screen display 34, which displays information to the user and provides a user interface for the user to input data, modify the basal rate, and trigger extraordinary bolas doses.

As well as wirelessly controlling the pump, the handset 3 also has an integral blood glucose meter 32. The blood glucose meter 32 detects the amount of glucose in the patient's blood. The blood may be analysed at the meter 32 by pricking the patient's finger and depositing a droplet of blood on a slide, which is inserted into the meter 32. The detected blood glucose level can be brought to the attention of the patient on the handset 3, and the patient can decide to trigger a bolas dose based on the blood glucose information. The result of every blood glucose test is automatically logged by the software and becomes immediately available for reference via the server 4 to the patient, medical professionals and even family members (such as parents). More generally, the handset 3 runs various software applications which help the user (and other authorised parties) to keep track of diet, insulin, blood glucose and exercise (which as explained above is recorded automatically from a sensor in the delivery device). By automating data collection, the handset 3 eliminates, or at least reduces, the need for a diabetes journal and ensures that comprehensive and accurate clinical information are constantly available to the patient and medical professionals via the server 4.

When controlling the delivery device, the handset 3 sends wireless signals to the delivery device 2 to deliver regular periodic doses of insulin at a pre-determined basal rate, which is set on the handset 3 according to the recommendations of a medical professional. The basal rate may be adjustable by the user within certain constraints. However, the software is configured such that it is not allowed for the basal rate to be adjusted remotely by third parties such as doctors. The hand-held device 3 also allows the user to trigger extraordinary bolus doses, for example after eating carbohydrates or performing exercise. As with a basal dose, the bolus dose is delivered by the delivery device 2 in response to control signals sent wirelessly from the handset 3. The user is able to input the volume of carbohydrates which have been consumed at a relevant time and is also able to input periods of exercise and the hand-held device is able to recommend adjustments to the basal rate or when a bolus is needed. As discussed above, the glucose monitor 32 may have an influence on the dosage. All of this information is transmitted to the server 4. The hand-held device 3 also receives information from the delivery device 2, for example to indicate whether it is faulty or when the insulin cartridge needs to be replaced. It also provides an indication of battery level.

Server

It will be understood from the above that the handset 3 and the delivery device 2 monitor and record clinical information while delivering insulin according to the body's needs. By providing this information to the server 4, it can be made almost immediately available to all those who need to see it. In particular, a mobile connection to a secure online management portal makes it possible for patients, clinicians and parents to be made constantly aware of, and able to react to, changing conditions. A diabetes clinic with patients using the system is able to see the current status of all its patients on a single screen, delivered to the clinic in real time. The portal can be accessed over the Internet in the clinic or through a smartphone. In addition to making it possible for a patient to access their latest clinical information online, it is possible for the patient to see simple visual analysis of their data, for example to identify trends and patterns in their blood sugar, and to immediately see their insulin dosing habits. This information can all be viewed using a simple online web portal that can be accessed from home, from work or from a smartphone. The server can also transmit SMS messages to a child's parents to let them know their child's information and state of health.

A patient using the system is provided with a personal login to the secure mobile diabetes management portal. Once logged in the patient can see all of their automatically collected data in the form of charts and graphs to help them understand where they might need to make adjustments. Exercise habits are mapped out in pie charts. An indication of exactly how and when the patient's insulin was delivered is provided. The patient's clinicians are able to see the same analysis and information, enabling them to call or text the patient whenever needed with guidance and advice.

From a single online dashboard screen, the clinic has access to the status of all the patients on the system; including current blood sugar, average blood sugar, insulin dosing, hypo frequency and blood testing habits. At a glance, anyone having difficulties can easily be identified for an immediate response. With a single click, all the data for a patient is analysed and charted to identify trends, patterns and problems. Using the portal, clinics can completely reorganise the way in which patients are managed. Text and email can be used to check on recent events. Clinic visits are focused completely on current and accurate information.

Cartridge Structure and Occlusion Detection

Figure 4A:
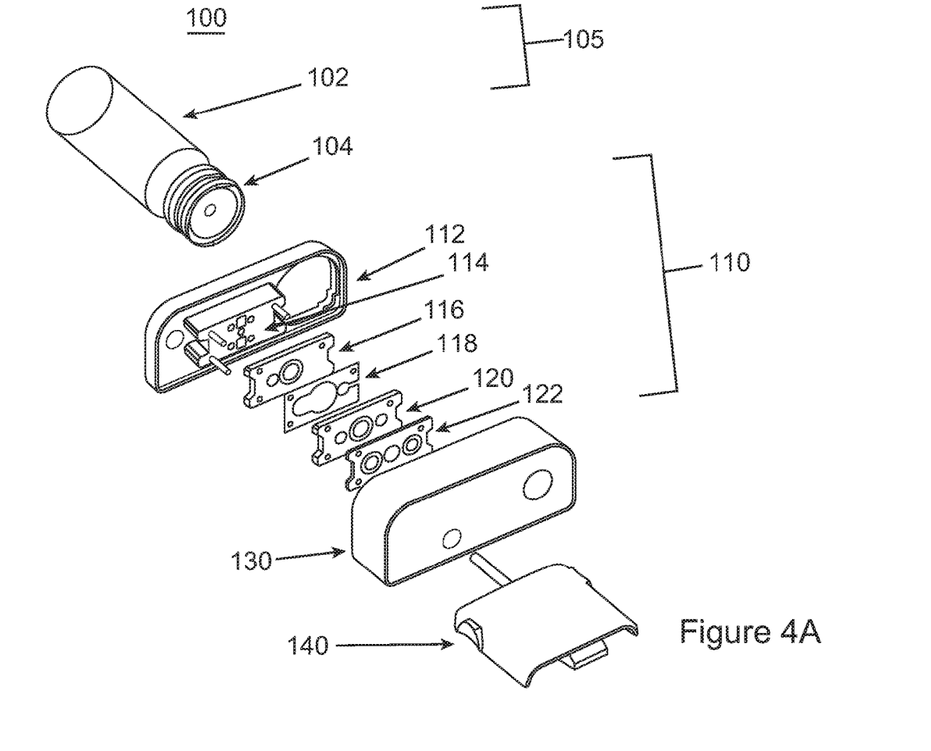
FIGS. 4A and 4B schematically illustrate exploded view of an insulin cartridge as a whole and an actuator assembly.

Referring to FIG. 4A, a schematic exploded view of the structure of a disposable cartridge 100 is provided. From top left, the cartridge 100 comprises a reservoir assembly 105. The reservoir assembly 105 comprises a reservoir 102 and a plunger assembly 104. The cartridge 100 also comprises a pump stack 110. The pump stack comprises an actuator assembly 112, a piston 114, a gearing/seal membrane 116, an occlusion layer 118, a fluidic layer 120 and a fluidic membrane 122. The cartridge 100 further comprises a housing assembly 130 and an infusion set 140.

Figure 4B:
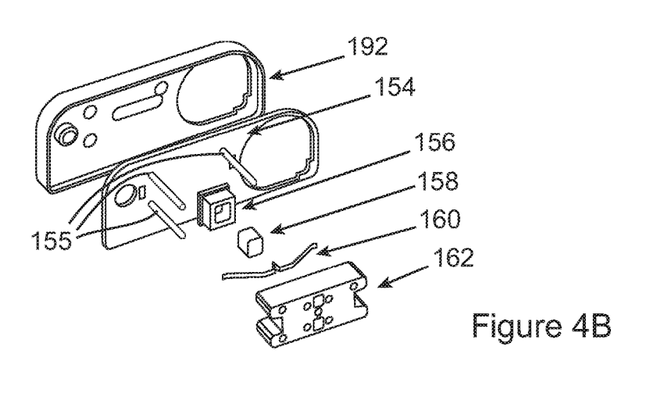

Referring to FIG. 4B, a schematic exploded view of the structure of the actuator assembly 112 is provided. From top left, the actuator assembly 112 comprises a base 152, a PCB (circuit) layer 154 from one side of which protrudes three conductive pins 155, an actuator insert 156, a block of wax 158, a diode assembly 160, and an actuator body 162.

In use, the reservoir 102 stores the insulin (or other therapeutic product) which is to be delivered to the patient's body, and the plunger assembly 104 is urged inwardly of the reservoir 102 by a biasing member on the main body of the delivery device, onto which the cartridge 100 is fitted. It will be understood that the reservoir 102 is generally cylindrical in shape, and the plunger 104 forms a moveable base end of the cylinder. The other end of the cylinder is formed by an internal structure of the housing assembly 130. The pressure applied by the plunger 104 on the insulin in the reservoir 102 pressurises the therapeutic product in the reservoir 102. When assembled, the reservoir 102 is received through an aperture in the base 152 of the actuator assembly 112 to engage with the housing assembly 130, which provides a channel for carrying the therapeutic product from the reservoir 102 under the pressure exerted by the plunger 104 through the fluidic membrane 122 and into a pumping chamber within the fluidic layer 120. From the pumping chamber, the insulin can be pumped in a controlled manner (under the influence of the piston 114) out to the infusion set 140, again via a channel in the housing assembly 130. The housing assembly 130 also has a channel for carrying insulin to the occlusion layer 118 when there is a blockage preventing the insulin exiting via the infusion set 140. The fluidic layer 120, fluidic membrane 122 and part of the housing assembly 130 form a valve arrangement. This valve arrangement comprises the pumping chamber, an inlet valve through which insulin passes from the reservoir 102 to fill the pumping chamber, an outlet valve through which insulin passes when the pumping chamber is compressed by the piston 114 causing the insulin to be expelled from the pumping chamber and out through the outlet valve, and a breakthrough valve through which the insulin is forced in the event of a blockage between the outlet valve and the delivery site on the patient. The fluidic membrane 122 comprises silicone membranes which are stretched over mesa structures in the fluidic layer 120, forming one-way valves by way of the mechanism described in US2010/0137784 (for example). The gearing membrane 116 is disposed between the piston 114 and the pumping chamber in the fluidic layer 120. The gearing membrane 116 both seals the pumping chamber and is displaced by the piston 114 on actuation to push liquid out of the pumping chamber and towards the outlet valve.

In FIG. 4B, the base 152 comprises an aperture through which the reservoir 102 is received to engage with the housing assembly 140, and a smaller slot aperture which exposes contact pads (not shown) on the PCB assembly 154 to the outside of the cartridge 100. Pins on the device body of the delivery device can therefore access the contact pads to provide an electrical connection between the two parts of the delivery device. The base 152 also comprises lugs (not shown) which are able to be inserted into the device body to engage with clips inside the device body to hold the two parts of the delivery device together. On the other side of the PCB assembly 154 are the conductive pins 155. These extend away from the PCB assembly (circuit layer) 154 through the various layers of the cartridge 100 described above. The conductive pins in the present embodiment extend to engage with the housing assembly 140, and therefore pass through all interior layers of the cartridge 100. These conductive pins effectively serve three purposes. Firstly, they properly align the layers of the cartridge 100 at the point of assembly, and ensure that they do not come out of alignment when the cartridge is in use. Secondly, they provide a conductive route between the PCB assembly 154 and the occlusion layer 118, these layers otherwise being sealed away from each other by the gearing membrane 116. In the case of a blockage, as explained above the insulin exiting the outlet valve is routed to the occlusion layer 118 via a breakthrough valve. In particular, the insulin is routed to a detection region comprising two contact points, each contact point being electrically connected to one of the conductive pins 155 (the third conductive pin being for structural purposes only). The presence of insulin at the detection region bridges the gap between the two contact points, thereby completing a circuit via the conductive pins to the PCB assembly 154, resulting in detection of the blockage at the PCB assembly 154 (or at control circuitry within the device body, which is electrically connected to the PCB assembly 154 via the contact pads), which may result in the sounding of an alarm on one or both of the delivery device and the handset. Thirdly, in the case of a leak permitting insulin to breach its designated channels through the various layers between the gearing membrane 116 and the housing assembly 130, the leaked insulin may spread out to electrically connect together the conductive pins (directly, at any one or more layers), thereby triggering an alarm as if a blockage had been detected.

The actuator assembly 112 also comprises an actuator insert 156 which is mounted to the PCB assembly 154 and receives a block of wax 158. A diode assembly 160 is provided, which includes a diode which will be embedded within the wax 158, and a conductive element for connecting the diode to the PCB assembly 154. The actuator insert 156, the wax 158 and the diode assembly 160 are trapped on assembly by the actuator body 162, which is received on the conductive pins 155, and which is able to receive the piston 114 as shown in FIG. 4A.

Figure 5:
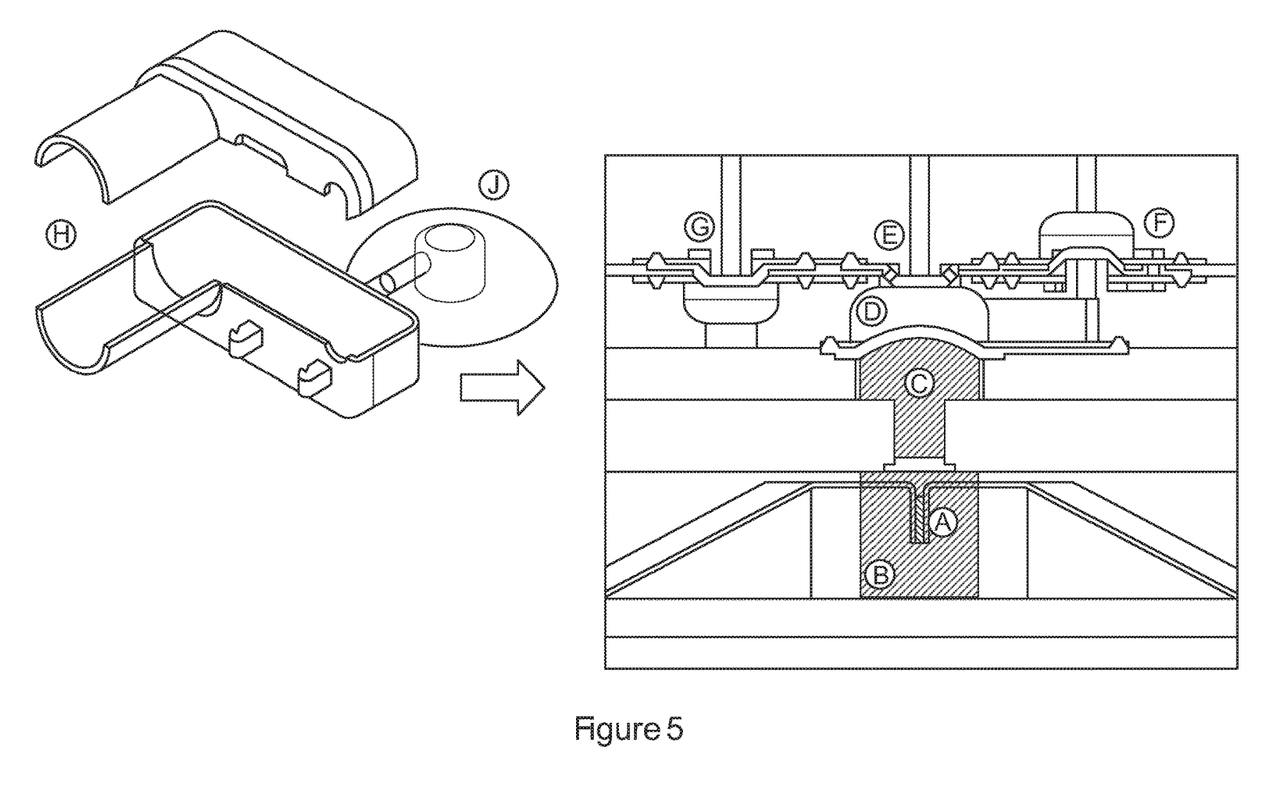
FIG. 5 schematically illustrates a cross section through an insulin cartridge, exposing the layered structure.

FIG. 5 schematically illustrates a cross section through the cartridge 100. In the cross section, a diode A is shown embedded within wax B. The wax B is sealed into the actuator insert by the actuator body, which sits above it. A piston C extends from proximate the wax B (the piston C being separated from the wax B by a first flexible membrane) to a second flexible membrane which separates the piston from a pumping chamber D. The pumping chamber D is fed insulin by a reservoir H via an inlet valve E. An outlet valve F is arranged to allow insulin from the pumping chamber to exit under the pumping action of the piston C. An occlusion (breakthrough) valve G is provided which, as discussed previously, allows insulin to pass through it when there is a blockage between the outlet valve F and the infusion site on the patient, for example within infusion set J. It will be appreciated that the valves E, F and G are formed by the sandwiching of the components 120, 122 and 130 of FIG. 4A.

Figure 6A:
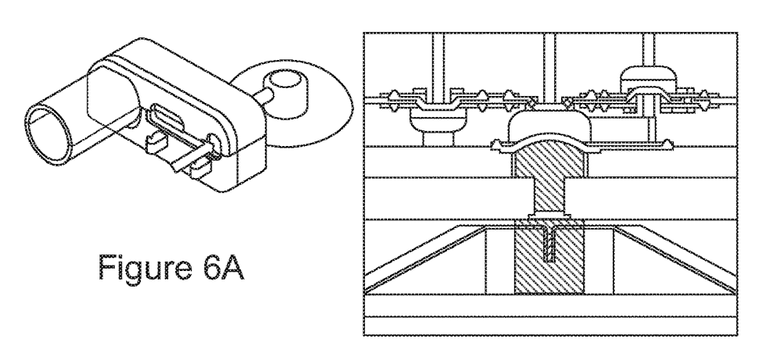
FIGS. 6A to 6F schematically illustrate the pumping operation of the insulin cartridge.
Figure 6B:
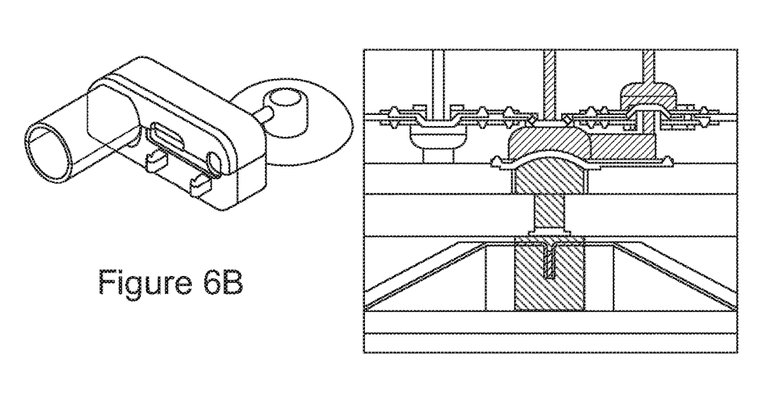
Figure 6C:
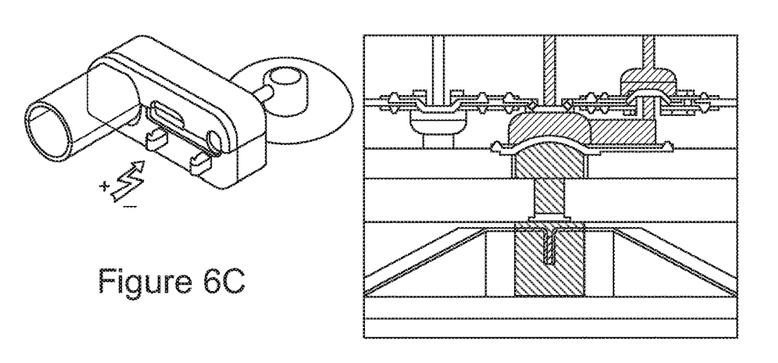
Figure 6D:
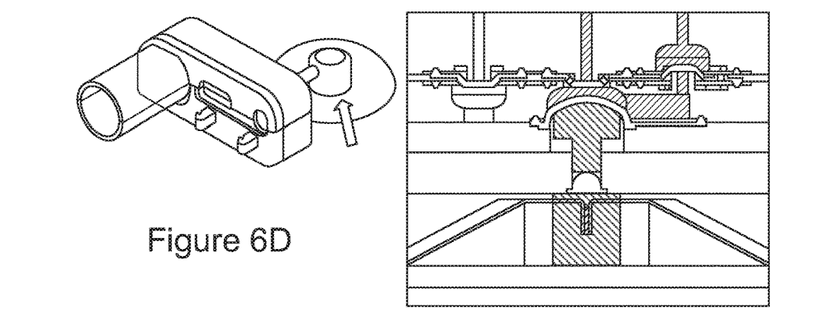
Figure 6E:
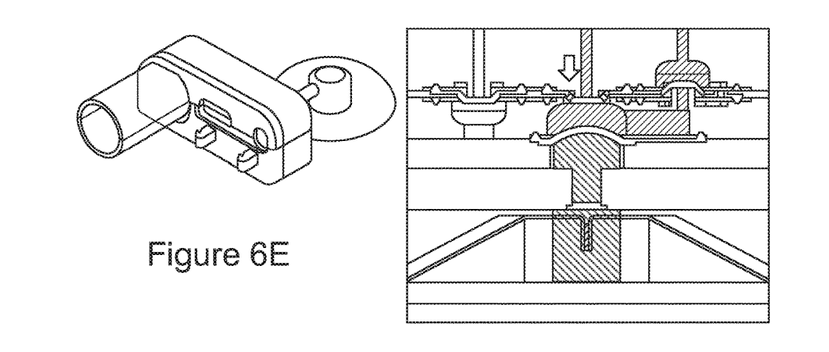
Figure 6F:
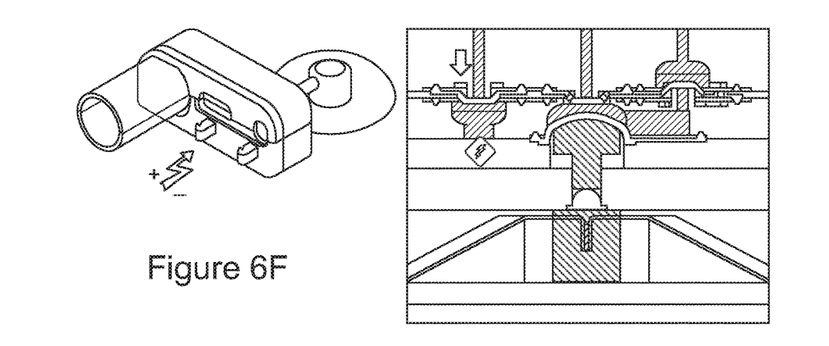

FIGS. 6A to 6F schematically illustrate the operation of the cartridge of FIG. 5. In FIG. 6A, a syringe and needle is used to pierce a septa in the base of the cartridge and fill the cartridge. Initially, the insulin fills the reservoir H. Referring to FIG. 6B, once the reservoir is full, the liquid progresses through the pumping chamber D. The liquid continues through the valves to prime the infusion set J. To start pumping the insulin, an electric current is applied, as shown in FIG. 6C. This causes the diode A to heat up, melting the wax B, which causes the wax B to expand. In FIG. 6D, it can be seen that the wax expansion pushes the piston C into the pumping chamber D, reducing the capacity of the pumping chamber D and causing the insulin in the pumping chamber D to be displaced towards the outlet valve F (it will be appreciated that the insulin cannot exit the pumping chamber D through the inlet valve E, since the valve only permits the passage of fluid in one direction—into the pumping chamber). The liquid is therefore forced through the one-way outlet valve F to the infusion site via the infusion set J. In FIG. 6E, the electric current has been discontinued, allowing the diode and the wax to cool and contract, consequently permitting the piston C to move back out of the pumping chamber D to its original position. It will be appreciated that one or more of the membrane between the wax and the piston, the membrane between the piston and the pumping chamber, and the pressure applied by the fluid in the reservoir through the inlet valve E and into the pumping chamber, may provide a bias to the piston C to keep it in its original position except for when the expansion of the wax B overcomes the bias. When the piston C returns to its original position, the pumping chamber D refills with liquid through the one-way inlet valve. This completes the pumping cycle. FIG. 6F demonstrates what happens if there is an occlusion during the pumping action. In FIG. 6F, as with FIG. 6C, an electric current is applied to the diode to heat the wax B and move the piston C into the pumping chamber D. The fluid from the pumping chamber D is forced through the outlet valve F, as with FIG. 6D, but in this case there is a blockage preventing the fluid from reaching the infusion site. This causes a build-up in pressure to the one way breakthrough (occlusion) valve G sufficient for the fluid to be redirected through the occlusion valve G to be conveyed to a detection region (on the occlusion layer 118 as discussed above).

Figure 7A:
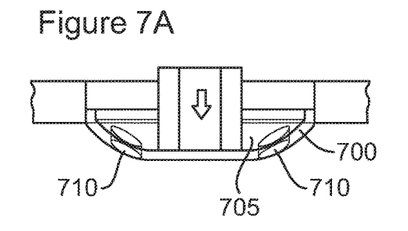
FIGS. 7A to 7C schematically illustrates the structure and operation of the one way valves used in the insulin cartridge.
Figure 7B:
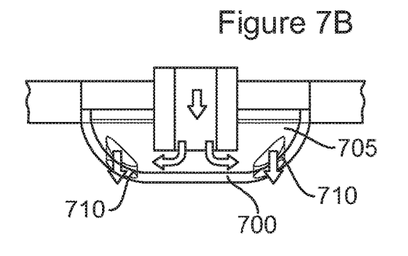
Figure 7C:
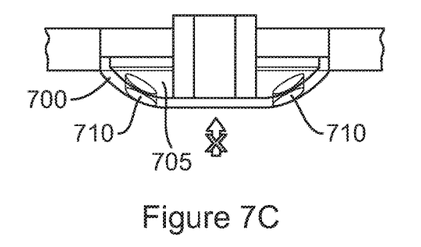

Referring to FIGS. 7A to 7C, the structure and operation of the one-way valves used for each of the inlet valve, the outlet valve and the occlusion valve are schematically illustrated. In FIG. 7A, liquid is under pressure at the inlet of the valve in a first direction (the direction of the arrow). The pressure of the liquid in FIG. 7A is insufficient to open the valve and allow the liquid to pass through. In FIG. 7B, the pressure is increased, and is now sufficient to deflect a membrane 700 away from the mouth of the inlet, allowing the liquid to enter into a chamber 705. The membrane 700 comprises apertures 710 which then allow the liquid in the chamber 705 to exit the valve. It is this mechanism which allows liquid to pass through the valve in a first direction (following the direction of the arrows through the valve as shown in FIG. 7B), subject to pressure at the inlet being sufficient. In the case of the three valves in the cartridge 100, the pressure required may be the same or different for each of these. Referring now to FIG. 7C, liquid is under pressure at the outlet to the valve (attempting to flow in the direction of the arrow). While this liquid can enter the chamber 705 through the apertures 710 in the membrane 700, it is unable to pass through the portion of the membrane which is seated on the inlet, and therefore the liquid cannot pass through the valve in this direction. This valve mechanism is described in detail in US2010/0137784.

Figure 8A:
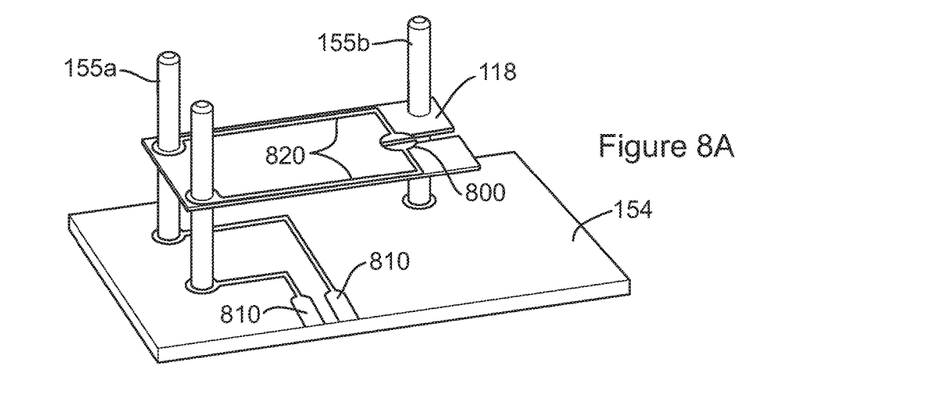
FIGS. 8A and 8B schematically illustrate an occlusion layer in electrical and structural connection with a PCB via conductive pins.
Figure 8B:
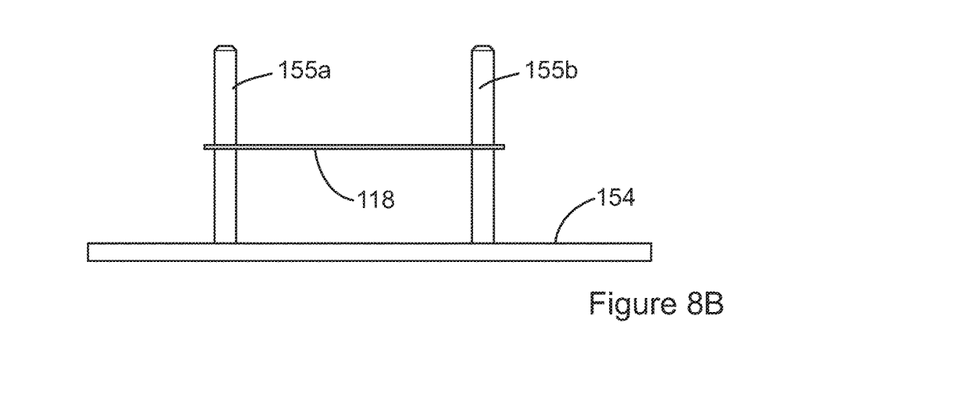

Referring now to FIGS. 8A and 8B, the occlusion layer 118 is shown mounted to the PC layer 154 via two conductive pins 155a, and a pin (which need not be conductive) 155b. Each of the conductive pins 155a is electrically connected to a conductive track 810 on the PCB layer 154 which connects it to detection circuitry. On the occlusion layer, each of the conductive pins 155a is electrically connected to a conductive track 820. The two conductive tracks terminate near each other at a detection region 800. The presence of insulin in the detection region 800 bridges the (air) gap between the two termination points, completing the electrical connection with the detection circuitry. It will be appreciated that, in the interests of clarity, the remaining layers and other components of the cartridge are omitted from FIGS. 8A and 8B.

While embodiments of the present invention have been described with reference to an insulin delivery system, it will be appreciated that the present invention may be applied instead to the delivery of other drugs.

The invention claimed is:

1. A therapeutic product delivery device, comprising:
   a circuit layer;
   an actuator layer carrying an actuator;
   an occlusion detection layer;
   a valve layer, through which a therapeutic product is conveyed by an action of the actuator;
   a plurality of conductive pins extending from the circuit layer through or to each of the actuator layer, the occlusion detection layer and the valve layer, the conductive pins aligning the layers with each other;
   wherein the occlusion detection layer comprises a plurality of contacts, each electrically connected to a respective one of the conductive pins, the contacts being provided at a detection region at which the therapeutic product is deposited in an event of a blockage; and
   wherein the blockage inhibiting the therapeutic product from being conveyed to the patient is detected when therapeutic product deposited in the detection region provides an electrical connection between the contacts.

2. The therapeutic product delivery device according to claim 1, wherein the valve layer comprises an outlet valve via which the therapeutic product is required to pass to reach the patient, and a break-through valve through which the therapeutic product is only able to pass in the event that the blockage inhibits the therapeutic product from reaching the patient, the therapeutic product passing through the break-through valve being deposited at the detection region.

3. The therapeutic product delivery device according to claim 2, wherein the break-through valve is disposed in series with, and at the exit of, the outlet valve.

4. The therapeutic product delivery device according to claim 2, comprising a channel for carrying the therapeutic product from the break-through valve to the detection region.

5. The therapeutic product delivery device according to claim 1, wherein a control circuitry is responsive to therapeutic product being detected in the detection region to trigger an alarm at the therapeutic product delivery device and/or at a control device.

6. The therapeutic product delivery device according to claim 1, wherein a control circuitry is responsive to therapeutic product being detected in the detection region to discontinue the operation of the actuator.

7. The therapeutic product delivery device according to claim 1, wherein the occlusion detection layer and the valve layer are sealed from the circuit layer by a seal layer.

8. The therapeutic product delivery device according to claim 1, comprising a reservoir for storing the therapeutic product, and wherein the valve layer comprises a pumping chamber from which the therapeutic product is pumped by action of the actuator, and wherein the pumping chamber is refilled from the reservoir via an inlet valve.

9. The therapeutic product delivery device according to claim 1, wherein the circuit layer, the actuator layer, the occlusion detection layer and the valve layer are disposed in this order.

10. The therapeutic product delivery device according to claim 1, wherein the delivery device comprises the circuit layer, the actuator layer, the occlusion detection layer and the valve layer in a cartridge part, and wherein the delivery device comprises a device body part comprising a battery and a control circuitry for applying an electric current to the actuator via the circuit layer, the cartridge part and the device body part being releasably engageable with respect to each other.

* * * * *